United States Patent [19]

Salibello et al.

[11] Patent Number: 5,191,367
[45] Date of Patent: Mar. 2, 1993

[54] INSTRUMENT AND METHOD FOR USE IN OPTOMETRIC EXAMINATIONS

[75] Inventors: Cosmo Salibello; Jonathan G. Torrey, both of Portland, Oreg.; Steven G. Coffman, Bothell, Wash.; Gerald M. Murch, Cupertino, Calif.

[73] Assignee: Applied Vision Concepts, Inc., Portland, Oreg.

[21] Appl. No.: 665,903

[22] Filed: Mar. 7, 1991

Related U.S. Application Data

[63] Continuation-in-part of Ser. No. 282,596, Dec. 12, 1988, Pat. No. 4,998,820.

[51] Int. Cl.$^5$ ............................................. A61B 3/02
[52] U.S. Cl. .................... 351/243; 351/203; 351/239
[58] Field of Search ............... 351/203, 233, 239, 240, 351/243, 246

[56] References Cited

U.S. PATENT DOCUMENTS

| | | | |
|---|---|---|---|
| 2,282,494 | 5/1942 | Potter. | |
| 4,212,520 | 7/1980 | Klimsa. | |
| 4,421,392 | 12/1983 | Crick et al. | 351/224 |
| 4,611,893 | 9/1986 | Schrier | 351/239 |
| 4,764,007 | 8/1988 | Task | 351/243 |

Primary Examiner—Rodney B. Bovernick

[57] ABSTRACT

An optical instrument for use in conducting optometric examinations which generates an alphanumeric type display simulating the optical features of displays provided by video display terminals. The instrument comprises a light source and a multi-layered screen through which light from the source may be transmitted. The screen employs light from the source in forming characters which are comprised of pixel-like light elements similar to those making up VDT generated characters. Further, the screen is operative for degrading the image quality of the characters by transforming the light elements into Gaussian type spatial profiles typical of the pixels generated by VDTs.

15 Claims, 2 Drawing Sheets

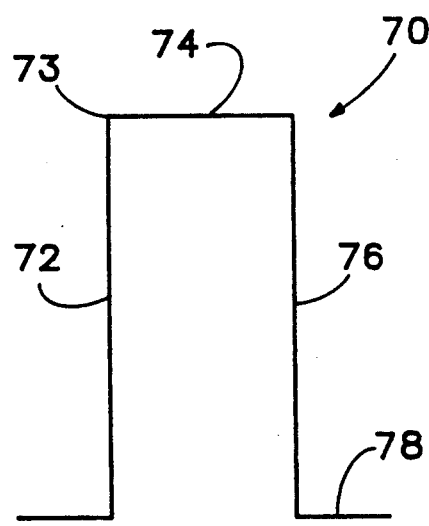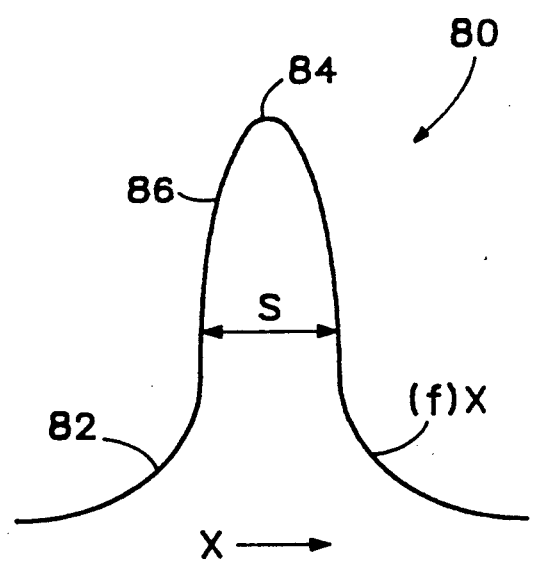
FIG. 5A (PRIOR ART)
FIG. 5B

INSTRUMENT AND METHOD FOR USE IN OPTOMETRIC EXAMINATIONS

This application is a continuation-in-part of co-pending application Ser. No. 07/282,596, filed Dec. 12, 1988, now U.S. Pat. No. 4,998,820.

BACKGROUND OF THE INVENTION

The present invention relates to vision testing equipment and more specifically to instruments and methods for use in conducting optometric examinations.

As the use of video display terminals has become more widespread, so too have certain ophthalmological afflictions associated with their utilization. The alphanumeric characters displayed on video screens are made up of dots or pixels which do not have well defined borders and therefore are difficult for the eye to focus upon. Further, since video screens are maintained at a constant distance of about 50 cm from the user's eyes, the same eye muscles are in constant use in focusing on the screens. These factors cause significant amounts of stress and fatigue on the eyes of video display terminal users which are often aggravated by the fact that many such users utilize their equipment for extended periods on a day after day basis. The stress associated with video display use frequently results in peculiar types of eye problems requiring special corrective prescriptions in the spectacles selected for the users afflicted with these problems.

In order to accurately diagnose these problems, appropriate test equipment and test procedures must be provided. In accordance with the process currently used by medical practitioners to determine the spectacle requirements of typical patients, an apparatus is placed in front of the eyes of the patient which enables the doctor to rapidly change a wide selection of lenses while the patient views a set of test images through the lens changing apparatus. As the patient focuses on the test images, the doctor assesses the status of the muscles inside the patient's eyes and judges their degree of relaxation through the use of a retinoscope. The doctor determines the combination of lenses and the prescription best suited to the patient by changing the lenses until he detects the combination which provides the most relaxed state in the eye muscles of the patient.

As may be understood from the above, the fitting of corrective lenses is basically a trial and error process in which the doctor observes the reaction of the patient's eye muscles to an appropriate test image for different combinations of lenses. However, without a test image which accurately simulates the conditions under which the patient may experience eye problems, a prescription for suitable corrective lenses may not be reliably determined. When presented with an image which does not have sharply defined edges or which is slightly out of focus, the eye will respond by reverting to a level of tonic muscle activity known as the resting point of accommodation, having a focal length which may be different than the focal length with a sharply defined image placed at the same distance from the eye. Accordingly, the prescription required for eyeglasses used with a video display terminal can differ from a prescription for use in viewing printed material.

Currently available equipment does not provide a satisfactory system for generating test images which simulate the characteristics of video display terminals. Consequently, most medical practitioners have been left with no recourse except to make educated guesses as to the lens corrections which may work best for their patients and to have their patients go back to work and try the new prescription out. This is, however, a time consuming, expensive, inaccurate and generally unsatisfactory method of proceeding to provide spectacle prescriptions.

It is therefore an object of the present invention to provide an improved system for testing the vision of video display terminal users which allows for accurate determination of the best corrective lens prescriptions for such patients.

It is another object of the present invention to provide an improved apparatus which accurately simulates alphanumeric characters as presented on a video display screen and which can be conveniently used in accordance with current optometric test procedures.

It is a further object of the present invention to provide an improved optometric instrument for use in determining prescriptions for corrective lenses which is economical, compact and simple to use.

SUMMARY OF THE INVENTION

The present invention comprises an optical instrument for use in optometric examinations which simulates the optical features of alphanumeric displays provided by video display terminals. The instrument comprises a light source such as a group of incandescent bulbs and a multi-layered screen through which light from the source may be directed to a patient viewing the screen. The screen comprises a printed layer including sets of small openings or pixels which cooperatively define alphanumeric characters in terms of multiple pixel-like elements of light from the light source. The screen further comprises a mechanism for degrading the alphanumeric character images by reducing the higher spatial frequencies of light associated with the light elements which define the characters.

In the preferred embodiment, the screen includes a lensing structure made of layers of plastic sheet materials having different indexes of refraction which refract the light from the light elements and provide said light elements with Gaussian profiles typical of the pixels formed by video display terminals in defining display characters. The preferred embodiment also includes a layer of diffusing material located adjacent the light source, functional in uniformly dispersing light from this light source. In operation, the light elements and lensing structure work together to generate an alphanumeric character display which accurately simulates the characteristics of the displays provided by video display terminals.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 3 is a cross sectional side view of the apparatus shown in FIG. 1 illustrating the operative components associated with the present invention;

FIG. 5A is a graphic illustration of a square-wave light amplitude produced by printed matter and crt simulation devices of the prior art; and FIG. 5B is a graph of a Gaussian light amplitude output produced by a video display terminal and by the present invention.

DESCRIPTION OF THE PREFERRED EMBODIMENT

Figure 1:
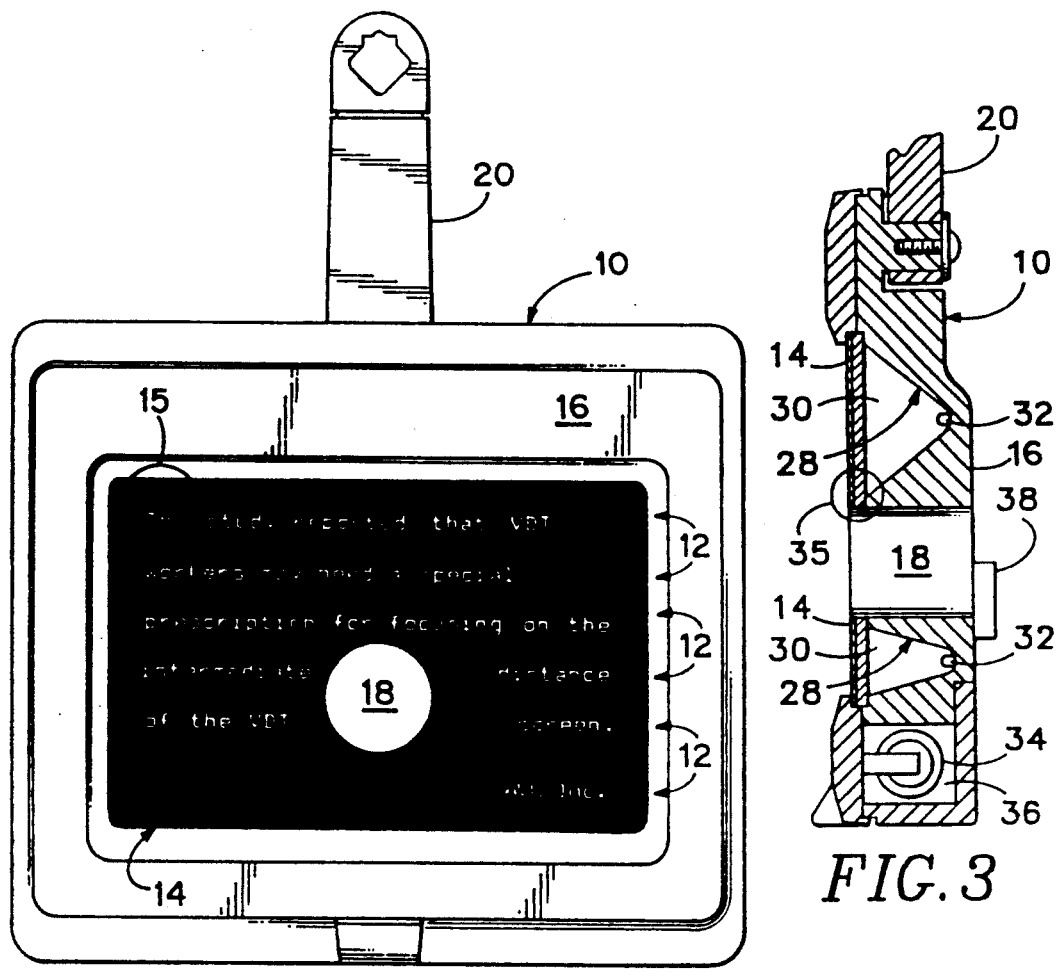
FIG. 1 is a front view of an apparatus corresponding to one embodiment of the present invention showing a display of alphanumeric characters in accordance with the invention.
Figure 2:
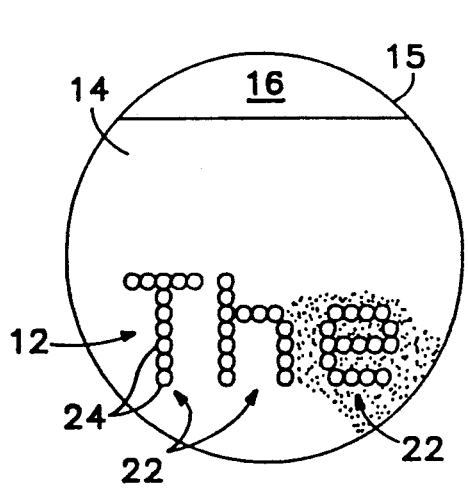
FIG. 2 is an enlarged view of a group of alphanumeric characters from FIG. 1 illustrating the details of the construction of the characters which make up the display shown in FIG. 1.

Referring now to FIG. 1, the apparatus 10 for simulating a video display terminal ("VDT") constitutes one embodiment of the present invention in which six lines 12 of alphanumeric characters are provided for viewing by a patient during an optometric examination. The lines 12 are presented on a multi-layered screen 14 which is mounted in the frame 16. A viewing tunnel 18 allows the medical practitioner conducting the optometric exam to directly view the patient's eyes from behind the apparatus 10 during the course of the examination, while support arm 20 allows the apparatus 10 to be conveniently mounted and readily swung into position for use when desired. As shown by FIG. 2 which provides a close-up view of the region within circle 15 in FIG. 1, alphanumeric characters 22 are made up of sets of pixel-like elements 24 disposed in 7×9 matrices in a manner similar to the characters displayed on many video display terminals.

Referring now to FIG. 3, the VDT simulation apparatus 10 includes a cavity 30 which extends around the viewing tunnel 18 in a rectangular pattern. The cavity 30 is parabolically-shaped outwardly from the viewing tunnel 18, with a number of incandescent bulbs 32 being positioned within the cavity 30 at focus locations defined by the parabolic shape of the cavity 30. The bulbs 32 and the cavity 30 operate as a light source 28 which provides light directed forwardly through the screen 14. A battery 34 is mounted within a small chamber 36 and is connected to the bulbs 32 through the switch 38 and functions as the power source for the bulbs 32 such that illumination is provided to the screen 14 when the switch 38 is turned on.

Figure 4:
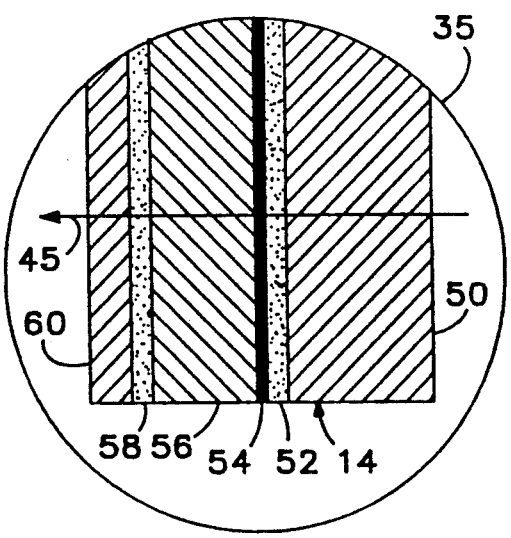
FIG. 4 is an enlarged cross sectional view of the multi-layered screen component of FIG. 3 illustrating the construction of the screen which is central to the functionality of the present invention.

Referring now to FIG. 4, providing a close-up view of the region within circle 35 in FIG. 3, screen 14 is comprised of a number of adjacent layers or sheets of material through which light from the source 28 as represented by the light ray 45 must pass in order to be emitted from the apparatus 10. In the preferred embodiment, the screen 14 includes six separate layers 50, 52, 54, 56, 58 and 60. Layer 50 comprises a 0.125 inch thick sheet of acrylic plastic having a "milky" appearance which acts to diffuse the light from the bulbs 32 and thereby assure more uniform illumination of the screen 14 while avoiding hot spots corresponding to the bulb positions. The layer 54 is comprised of a very thin film or mask of vinyl ink printed onto the back of layer 56. The layer 54 is applied via silk screen printing techniques in a pattern which is made up of sets of small circular openings or pixels which cooperatively define the alphanumeric characters 22. The layer 56 comprises a 0.020 inch thick sheet of polycarbonate plastic having a color which is appreciated by the normal human eye as a mid-saturation green hue, although any suitable color may be chosen to simulate the desired VDT color. The coloration of the layer 56 affects the light transmitted through the screen 14 and results in the transmitted light approaching the color of the light generated by excitation of the P31 phosphor commonly used in VDTs. The components of the screen 14 thus far described are bonded together by the layers 52 and 58 which may comprise a series of relatively narrow and widely spaced-apart strips of acrylic adhesive for physically separating or spacing the other layers of the screen 14 while joining them together. It should be noted that the layers 52 and 58 may largely comprise air spacing or, in a preferred embodiment, may comprise 2 mil acrylic adhesive (suitable 3M #967), and have a substantially lower index of refraction than the layer 56, leading to certain desirable optical effects hereinafter described. The final exterior layer 60 of the screen 14 comprises a 0.010 inch sheet of polycarbonate plastic functioning as a cover and providing an anti-glare surface for the screen 14. The exterior surface of the outer layer 60 carries a satin matte texture, which also contributes to the desired effect. The layer 60 is selected to be of sufficient thickness to function in combination with other layers 50, 52, 56 and 58 to attenuate the light forming the characters 22 to the extent required to provide approximately a 3 to 1 contrast ratio between the characters and their surrounding background in a manner similar to the contrast found in VDTs. The contrast may also be adjusted by varying the intensity of the light source 28.

Printed characters produce a square-wave light amplitude curve as illustrated in FIG. 5A, if the character is scanned across, and the light amplitude curve of prior art devices which rely on printed pixels to simulate a crt is substantially the same.

FIG. 5A illustrates a square-wave light amplitude produced by printed matter such as an eye chart. As shown in the figure the light amplitude rises instantaneously from an initial level, corresponding to the background or the paper in the case of printed matter, it rises initially along a path 72 to a light amplitude level 74. The rise in light amplitude 72 corresponds to the edge of a printed character, i.e., the transition from blank paper to ink. The horizontal portion 74 represents a constant light amplitude level across the width of a character or a dot of ink. It may be observed that the corner 73 of the waveform corresponds to the sharp transition between the paper and the ink. At the opposite edge of the character, i.e., where the ink stops, the light amplitude falls along a vertical path 76 to the initial or background light amplitude level indicated by horizontal line 78.

FIG. 5B is a graph of a Gaussian light amplitude output provided by a video display terminal, and by the present invention. This curve may be generated by scanning an actual crt pixel with a micro scan light meter and corresponds to the following formula:

$$f(X) = \exp[-(4 l_n^2 X^2)/S^2]$$

where $l_n$ is the luminance of the pixel, S is the width of the pixel at half luminace maximum and X is the x-axis position of the meter.

Performing Fourier analysis then provides the amplitude and fundamental frequency of the function. The optical properties of each diffusing layer (for example as illustrated in FIG. 3) are known or may be determined based upon the material and thickness. The layer combination should have a Fourier transform which matches that actually measured for a selected crt.

FIG. 5B is a graph of a Gaussian light amplitude output produced by a video display terminal and by the present invention. It may be observed that the waveform of FIG. 5B has a peak amplitude 84 at the center corresponding to the center of a light spot or pixel, the center being the brightest location. Moving away from the center of the pixel, the light amplitude falls off along a shoulder 86, to a half luminance level indicated by the letter "S". Proceeding further away from the center of the pixel, the light amplitude again tapers off gradually along curve 82. The curve is symmetrical about the peak 84.

In operation, the exemplary design of the screen 14 illustrated in FIG. 3 provides optically unique characteristics on two levels. First, the pixels incorporated into the printed layer 54 allow the characters 22 to be formed from corresponding elements of light as transmitted through the screen 14. The characters 22 are thereby constructed of pixel-like elements of light in a manner analogous to characters displayed on VDTs. Second, since the layers 52 and 58 provide a lower index of refraction than the layers 56 and 60, the arrangement of these layers forms a lensing structure which operates to refract the light of the elements forming the characters 22 and reduce the higher order spatial frequencies associated with the light elements. Diffraction also occurs at the juncture of the polycarbonate plastic and the adhesive, scattering the light. The layers refract the light to a known degree, and the combination thereof provides the desired Gaussian light amplitude curve.

The light elements forming the characters 22 are effectively defocussed, wherein the borders of the characters 22 are "blurred" for degrading the quality of image provided by the apparatus 10. The layers are selected to provide amounts of refraction sufficient to transform the spatial distribution of the light comprising the individual pixel elements into Gaussian type profiles when viewed from a distance of approximately 50 cm from the screen 14, such Gaussian profiles being very similar to the Gaussian type profiles characteristic of the pixels generated by VDTs. The characters generated by VDTs are thus simulated in two important respects: through the use of pixel-like light elements, and by providing elements having an appropriately degraded image quality, employing a non-complex layer construction.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An optical system for use in conducting optometric examinations on patients who suffer from eye fatigue due to the use of VDT displays, said system comprising:
   (a) a light source;
   (b) pixel means including a predetermined pattern of small, circular openings through which light is transmitted from the light source toward the patient, for forming alphanumeric characters consisting of pixel-like light elements, each light element formed by one of said openings; and
   (c) a generally planar multi-layer screen disposed between the pixel means and the patient for reducing high-frequency components of the light elements such that the characters exhibit a substantially Gaussian light amplitude curve.

2. The system of claim 1 further comprising a milky plastic diffusion layer disposed between the light source and the pixel means for diffusing the light from said source in order to reduce optical hot spots associated with said source.

3. The system of claim 1 wherein said light source and the screen are selected so as to provide a contrast ratio of approximately 3 to 1 between said alphanumeric characters and their surrounding background.

4. The system of claim 1 wherein the screen includes a colored plastic layer (56) for providing a color to said pixel-like light elements which simulates the color of a VDT.

5. An optical display method for use in conducting optometric examinations comprising:
   transmitting light from a light source through a screen having sets of openings which function to cooperatively define alphanumeric characters in terms of pixel-like light elements; and
   degrading the quality of images provided by said light elements by selectively reducing the higher order spatial frequencies associated with the light transmitted through said openings so that light elements transmitted from the light source through the screen to the patient, measured by a suitable micro scan light meter, exhibit a light amplitude curve approximately described by the equation $f(X) = \exp[-(4L^2X^2)/S^2]$ where exp is natural exponentiation, L is luminance of the light element, X is the x-axis position of the light meter and S is the width of the light element at half luminance.

6. The optical display method of claim 5 wherein said step of degrading the quality of the image provided by said light elements includes the step of refracting and diffracting the light from these elements by passing this light through a lensing structure.

7. The optical display method of claim 5 wherein said step of degrading the quality of the image provided by said light elements includes the step of passing the light through a light transmissive layer having a matte textured surface.

8. The optical display method of claim 5 further including the step of diffusing said light prior to passing it through said light transmissive means in order to reduce hot spots associated with the light source.

9. The optical display method of claim 5 further including the step of altering the color of said light elements to simulate the color of a crt display.

10. An optical system for use in conducting optometric examinations on patients who suffer from eye fatigue due to the use of VDT displays, said system comprising:
   a light source; and
   a generally planar screen, arranged to receive light provided by the light source and transmit a portion of the received light toward the patient;
   pixel means in the screen, the pixel means including a predetermined pattern of small, circular openings through which the provided light travels from the light source toward the patient as a pixel-like light element, each light element being formed by one of said openings, for simulating VDT pixels; and means in the screen for refracting the light elements and reducing higher order spacial frequencies in the light elements such that the light elements exhibit a substantially Gaussian light amplitude curve to the patient to emulate light emitted by pixels in a VDT.

11. An optical system according to claim 10 wherein the screen includes a diffusion layer (50) exposed to the light source;

a polycarbonate cover layer (60) having an anti-glare surface; and a colored plastic layer (56) disposed intermediate the diffusion layer and the polycarbonate layer; and wherein the pixel means consists of a thin ink mask (54) formed onto a surface of the colored plastic layer (56) so that the colored plastic layer is substantially opaque except for the said circular openings.

12. An optical system according to claim 11 wherein the refracting means includes a first bonding layer (52) disposed intermediate the diffusion layer (50) and the colored plastic layer (56), the first bonding layer having a substantially lower index of refraction than the plastic layer (56), for refracting light transmitted through the pixel means so as to reduce higher-order spacial frequencies.

13. An optical system according to claim 12 wherein the refracting means further includes a second bonding layer (58) disposed intermediate the cover layer (60) and the colored plastic layer (56), the second bonding layer having a substantially lower index of refraction than the plastic layer (56), for refracting light transmitted through the pixel means so as to reduce higher-order spacial frequencies.

14. An optical system according to claim 12 wherein the diffusion layer (50), polycarbonate cover layer (60), colored plastic layer (56) and first and second bonding layers are selected to have optical properties such that in combination they provide the refracting means to reduce higher-order spacial frequencies so that light transmitted from the light source through the screen to the patient exhibits a substantially Gaussian light amplitude curve.

15. An optical system according to claim 12 wherein said diffusion layer, polycarbonate cover layer, colored plastic layer and bonding layer are selected so that light elements transmitted from the light source through the screen to the patient, measured by a suitable micro scan light meter, exhibit a light amplitude curve described by the equation $f(x) = \exp[-(4L^2X^2)/S^2]$ where exp is natural exponentiation, L is luminance of the light element, X is the x-axis position of the light meter and S is the width of the light element at half luminance.

* * * * *